United States Patent [19]

Abraham et al.

[11] Patent Number: 4,731,473
[45] Date of Patent: Mar. 15, 1988

[54] COMPOUNDS USEFUL IN TREATING SICKLE CELL ANEMIA

[75] Inventors: Donald J. Abraham, Murrysville; Otto W. Woltersdorf, Jr., Chalfont; Edward J. Cragoe, Jr., Lansdale, all of Pa.

[73] Assignee: Merck & Co., Inc., Rahway, N.J.

[21] Appl. No.: 848,078

[22] Filed: Apr. 4, 1986

[51] Int. Cl.⁴ .............................................. C07C 65/40
[52] U.S. Cl. .................................... 562/464; 562/463; 562/451; 560/53; 568/333
[58] Field of Search ..................... 562/464, 463, 451; 560/53; 514/570, 571

[56] References Cited

U.S. PATENT DOCUMENTS 3,255,241  6/1966  Schutz et al. ........................ 560/53
3,478,085  11/1969  Cragoe ................................. 560/53
4,070,539  1/1978  Cragoe ................................. 560/56

FOREIGN PATENT DOCUMENTS 998835  7/1965  United Kingdom .

OTHER PUBLICATIONS

E. J. Cragoe, Jr., Diuretics: Chemistry, Pharmacology and Medicine, John Wiley & Sons, New York, 1983, p. 213.

Primary Examiner—Paul J. Killos
Attorney, Agent, or Firm—Joseph F. DiPrima; Michael C. Sudol

[57] ABSTRACT

The present invention is directed to compounds of the general formula I and pharmaceutically acceptable salts thereof:

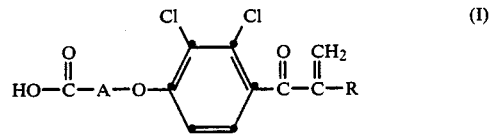

wherein:
R=ethyl, propyl or isopropyl; and
A=$(CH_2)_n$ wherein n is 2, 4 or 5, and $C(CH_2)_3$.

14 Claims, No Drawings

COMPOUNDS USEFUL IN TREATING SICKLE CELL ANEMIA

PRIOR ART

U.S. Pat. Nos. 3,478,085 and 3,255,241 and British Published application 998,835 disclose general structures which include the compounds claimed in the present invention. None of these references, however, specifically disclose the claimed compounds. E. J. Cragoe, Jr., Ed., *Diuretics: Chemistry, Pharmacology and Medicine,* John Wiley and Sons, New York 1983, discloses an analogue of the claimed compounds on page 213.

BACKGROUND OF THE INVENTION

This invention relates to compounds useful in treating sickle cell anemia and, more specifically, it relates to a method of resisting sickling of sickle hemoglobin in a sickle cell anemia patient.

Sickle cell anemia is a hereditary blood disease which primarily afflicts people of African, Mediterranean and Mideastern origin or their descendants. The anemia results from the physical aggregation of a mutant hemoglobin protein constituent, hemoglobin S, in red blood cells. This aggregation results in a distortion in shape of deoxygenated red blood cells and causes impairment of flow of the blood through the capillaries (sickle cell "crises"). As the principal function of hemoglobin is to transport oxygen from the lungs to body tissues, efficient flow of oxygen throughout the body's tissues is impeded by the anemia due to a lower number of red blood cells. Sickle cell anemia also may have an indirect effect on the heart, lungs, kidneys, spleen, bones and brain. Sickle cell anemia crises can be extremely painful, can result in infections such as pneumonia, can result in skin ulceration, can contribute to strokes and seizures in the afflicted individuals and can also result in the development of chronic bone infections.

In general, the result of the differences between cells containing hemoglobin A, the normal hemoglobin, and hemoglobin S, the sickle cell hemoglobin, is that in the deoxygenated state the former cell is generally flexible and biconcave discoid in shape, while the latter is more rigid and crescent shaped and typically has pointed ends. This rigidity and distortion in shape causes the cells to be lodged in the capillary. Hemoglobin molecules contain two beta polypetide chains and two alpha polypeptide chains. In the sickle cell hemoglobin, a mutation is present in the beta chains. More specifically, the sixth amino acid of each beta chain is changed from glutamic acid to valine. As a result of this mutation, hemoglobin S upon deoxygenation polymerizes and causes the cell to assume the elongated, sickle-like configuration. As the sickle cells have a much shorter life span than normal red cells, the body depletes the sickled cells more quickly thereby creating an anemic condition.

Electrophoresis is one of the well established laboratory tests employed in diagnosing sickle cell anemia. Electrophoresis tests determine whether an individual has sickle cell anemia (homozygous) or merely the sickle cell trait (heterozygous). The latter refers to an individual not having the disease but having the capability of transmitting the disease to offspring if mated to another heterozygote.

One major assay for evaluating antisickling agents involves measuring their effect on increasing the concentration at which sickle hemoglobin forms a gel. This is called the solubility or $C_{sat}$ assay.

Another well established laboratory test employed for determining the potential effectiveness of an antisickling agent is by determining the oxygendisassociation curve. When a graph is plotted of the percentage saturation of hemoglobin with oxygen (ordinate) against the partial pressure of oxygen, sometimes called the oxygen tension (abscissa) a characteristic sigmoid curve is obtained. With respect to the curve obtained with whole blood from normal adults, that obtained with whole blood from sickle-cell anemia sufferers is displaced to the right with a loss of sigmoidicity. That is to say, the hemoglobin in the sickle-cell erythrocytes appears to have a reduced oxygen affinity compared with that in the normal erythrocytes, a higher oxygen tension being required to produce a given percentage saturation. (With whole blood from individuals having the sickle-cell trait the curve is not significantly displaced from the normal).

The compounds of this invention are effective in both increasing sickle hemoglobin solubility toward more normal values ($C_{sat}$ assay) and in left-shifting (normalizing) the oxygen disassociation curve.

Treatment for the various complications which have resulted from sickle cell anemia are known and should be distinguished from prophylactic treatment which is unknown and would eliminate the occurrence of the complications and adverse symptoms. Currently, symptomatic treatment is available. For example, one can treat the symptoms by using analgesics for pain, or antibiotics for infection, but these approaches do not arrest the underlying sickling phenomena.

There remains, therefore, a very real and substantial need for a treatment method which minimizes the adverse consequences of sickle cell anemia by directly inhibiting the underlying cause of sickle cell crises.

The present invention has met the above-described need by providing a method which preferably involves administering to a person a therapeutically effective dosage of a compound of this invention. This dosage is administered by the compound being reacted extracorporeally with the patient's own blood or the agent may be given orally. In the former approach the agent is preferably administered to stored blood samples taken from patients and then the blood is readministered.

It is an object of the present invention to provide a method of treating a sickle cell anemia patient's blood so as to reduce undesired sickle cell crises.

It is another object of the present invention to provide an effective means for resisting undesired sickling of hemoglobin in sickle cell anemia patients.

DESCRIPTION OF THE INVENTION

The instant invention is directed to compounds of the general formula (I) and pharmaceutically acceptable salts thereof:

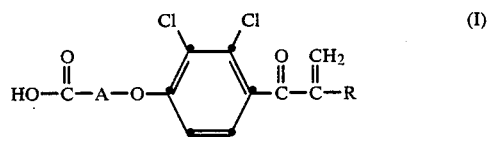

wherein:
R is ethyl, propyl or isopropyl; and
A is $(CH_2)_n$, $-C(CH_2)_3-$ and n=2, 4, or 5.

The present invention is also directed to an antisickling pharmaceutical carrier and an antisickling agent of the general formula (II) and pharmaceutically acceptable salts thereof:

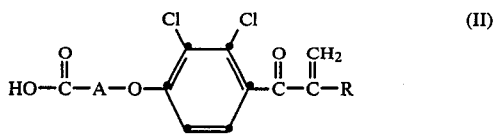

wherein:
R=ethyl, propyl or isopropyl; and
A=

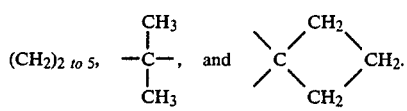

The compounds of the above formula as defined, may be used in medicine in the palliation of haemoglobinopathies and in particular for alleviating the symptons of sickle-cell anemia and mitigating the sufferings of those having the condition. The compounds may be used both on a regular maintenance basis and for the relief of acute crisis states.

The compounds may be administered to the human recipient by a route selected from oral, parenteral (including subcutaneous, intradermal, intramuscular and intravenous) rectal and extracorporeally. The size of an effective palliative dose of a compound will depend upon a number of factors including the identity of the recipient, the type of haemoglobinopathy involved, the severity of the condition to be treated and the route of administration and will ultimately be at the discretion of the attendant physician.

The compounds of Formula II are prepared as follows:

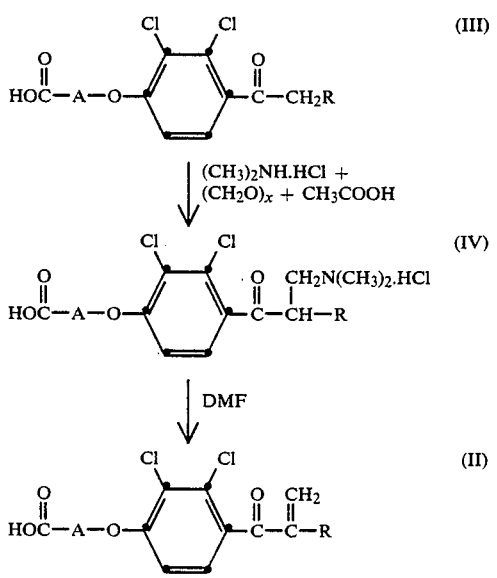

A compound of Formula III is reacted under the conditions of the Mannich reaction with dimethylamine hydrochloride, paraformaldehyde and a catalytic amount of acetic acid to form a compound of Formula IV. The reaction is generally conducted without a solvent at temperatures in the range of 100° C. for periods of 5 to 12 hours.

It is generally not convenient to isolate the compounds of Formula IV but to convert them directly to the desired products of Formula II by heating with a solvent, such as N,N-dimethylformamide (DMF) or 1-methyl-2-pyrrolidinone. The reaction is generally complete when heating at 75°-110° C. is carried out for 5-12 hours.

The intermediate compounds of Formula IIIa are prepared as follows for compounds where $$A = A' = -(CH_2)_3-, -(CH_2)_4-, -(CH_2)_5-, \text{ or } \diagdown C(CH_2)_3\diagup,$$

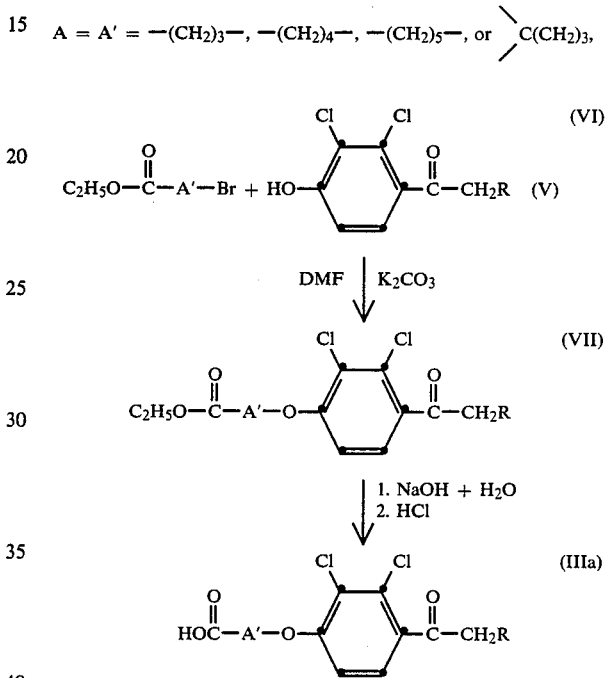

A phenol of Formula V is reacted with a bromo ester of Formula VI to produce an ester of Formula VII. The reaction is conducted in any one of several solvents, such as N,N-dimethylformamide (DMF) or 1-methyl-2-pyrrolidinone in the presence of a base, such as potassium carbonate or sodium carbonate. The reaction temperature is generally of 25° to 100° C., preferably at 55°-60° C. for a period of one to 48 hours, preferably 10-20 hours.

The esters of Formula VII are converted to the corresponding carboxylic acids of Formulla IIIa by saponification with aqueous sodium hydroxide followed by acidification. Saponification is conveniently conducted in the presence of the N,N-dimethylformamide solvent used for making the ester. Saponification is generally complete within one to five hours when the reaction temperature is in the range of 75°-100° C.

When A is $-(CH_2)_2-$, the compounds of Formula IIIb are prepared as follows:

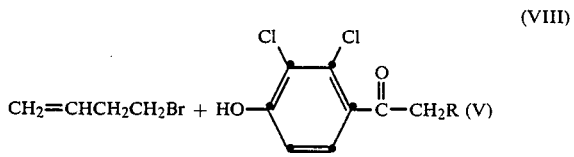

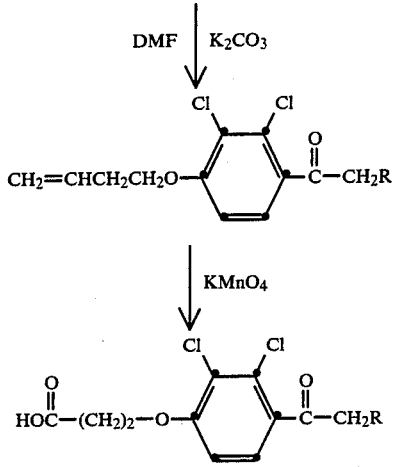

Reaction of a phenol of Formula V with 4-bromo-1-butene (VIII) in a solvent, such as N,N-dimethylformamide or 1-methyl-2-pyrrolidinone and a base, such as potassium carbonate or sodium carbonate gives ethers of Formula IX.

Compounds of Formula IX are converted to compounds of Formula IIIb by oxidation. The reaction is conducted by stirring a two-phase mixture of a compound of Formula IX in methylene chloride with an aqueous solution of potassium permanganate at a temperature of 0° to 10° C. for 30 minutes to 3 hours. A detergent, e.g., benzyltriethylammonium chloride is used to promote the two-phase reaction. The product is isolated by extracting the methylene chloride layer with aqueous sodium hydroxide followed by acidification of the aqueous extract with hydrochloric acid.

When A is —C(CH$_3$)$_2$— the compounds of Formula IIIc are prepared as follows:

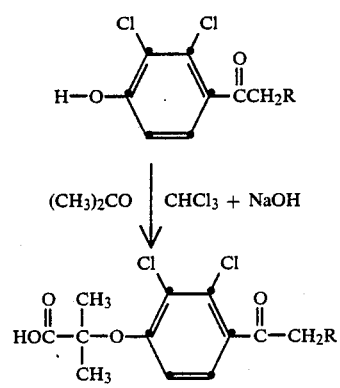

The reaction of a phenol of Formula V with acetone and chloroform in the presence of sodium hydroxide produces compounds of Formula IIIc. The reaction is conducted by adding chloroform dropwise to a mixture of a compound of formula V in acetone followed by refluxing the mixture for a period of 1 to 6 hours. The product is isolated by evaporating the acetone, treating the residue with water, acidifying the mixture, extracting with ether, drying the ether and removing the solvent. The product is conveniently purified by chromatography.

The salts of compounds of Formula I are also a part of the instant invention. These compounds are prepared by reacting the acids of Formula II with an appropriate base, for example, alkali metal or alkaline earth bicarbonate, carbonate or alkoxide, an amine, ammonia, an organic quaternary ammonium hydroxide, guanidine and the like.

The reaction is generally conducted in water when alkali metal bicarbonates or carbonates are used, but when alkoxides and the organic bases are used, the reaction may be conducted in an organic solvent, such as ether, ethanol, N,N-dimethylformamide and the like.

The preferred salts are the pharmaceutically acceptable salts such as sodium, potassium, ammonium and the like.

As implied earlier, the compounds of this invention may be administered by a variety of established methods, including intravenously, intramuscularly, subcutaneously, orally and extracorporeally. The precise mode of administration is left to the discretion of the practitioner. The option of extracorporeal administration is unique to the therapeutic approach of this invention. Since the entity to which therapy is administered is the erythrocytes of the patient, blood can be removed from the patient, treated with the drug and returned to the patient after the desired interaction between the drug and the erythrocytes has occurred. Before returning the drug-treated blood, the excess (unreacted drug) may be removed, thus reducing any ancillary effects that this excess might cause.

The compounds of formulae I or II are utilized by formulating them in a composition such as tablet, capsule or elixir for oral administration. Sterile solutions or suspensions can be used for parenteral administration. About 70 μg to 500 mg of a compound or mixture of compounds of formulae I or II, or a physiologically acceptable salt is compounded with a physiologically acceptable vehicle, carrier, excipient, binder, preservative, stabilizer, flavor, etc., in a unit dosage form as called for by accepted pharmaceutical practice. The amount of active substance in the composition is such that dosage in the range indicated is obtained.

Illustrative of the adjuvants which may be incorporated in tablets, capsules and the like are the following: a binder such as gum tragacanth, acacia, corn starch or gelatin; an excipient such as dicalcium phosphate; a disintegrating agent such as corn starch, potato starch, alginic acid and the like; a lubricant such as magnesium stearate; a sweetening agent such as sucrose, lactose, or saccharin; a flavoring agent such as peppermint, oil of wintergreen or cherry. When the dosage unit form is a capsule, it may contain in addition to materials of the above type a liquid carrier such as a fatty oil. Various other materials may be present as coatings or to otherwise enhance the pharmaceutical elegance of the preparation. For instance, tablets may be coated with shellac, sugar or the like. A syrup or elixir may contain the active compound, sucrose as a sweetening agent, methyl and propyl parabens as preservatives, a dye and a flavoring such as cherry or orange flavor.

Sterile compositions for injection can be formulated according to conventional pharmaceutical practice by dissolving or suspending the active substance in a conventional vehicle such as water for injection, a naturally occurring vegetable oil like sesame oil, coconut oil, peanut oil, cottonseed oil, etc., or a synthetic fatty vehicle like ethyl oleate or the like. Buffers, preservatives, antioxidants and the like can be incorporated as required.

Since an individual patient may present a wide variation in severity of symptoms and each drug has its unique therapeutic characteristics, it is up to the practitioner to determine the patient's response to treatment and vary the dosages accordingly. A recommended dose range is from 100 μg/kg to 15 mg/kg as a primary dose and then, if necessary a sustaining dose euqal to half to equal the primary dose may be administered every 12 to 24 hours.

When the compounds of this invention are employed for extracorporeal treatment of blood, it is generally convenient to use a water soluble salt of the compound which may be made isotonic by addition of sodium chloride. The concentration of the compound which is used for this purpose is generally in the range of 0.1 to 10 mM with a range of 1 to 3 mM being more commonly used.

The following examples are included to illustrate the synthesis of representative compounds of Formula II, the preparation of representative dosage forms and the preparation of sterile solutions for use in the extracorporeal treatment of the blood of patients with sickle cell anemia. It is intended that the specification and examples be considered as exemplary only, with the true scope and spirit of the invention being indicated by the claims of the invention.

EXAMPLE 1

Preparation of 3-[2,3-dichloro-4-(2-methylenebutyryl)phenoxy]propionic acid

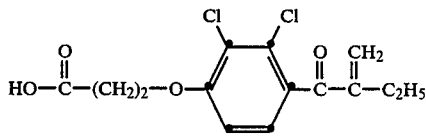

Step A:

2,3-Dichloro-4-(3-butenyloxy)butyrophenone

A mixture of 2,3-dichloro-4-butyrophenone (21 g, 0.090 mole) and potassium carbonate (37 g, 0.27 mole) in N,N-dimethylformamide (100 ml) were stirreed and heated to 60° C. 4-Bromo-1-butene (26.7 g, 0.2 mole) was added and the mixture stirred and heated at 60°–65° C. for five hours. The reaction mixture was poured into ice water and the mixture extracted with ether. The ether layer was washed with water and then with brine and finally dried over MgSo4. The ether was removed by evaporation at reduced pressure to give 25 g of 2,3-dichloro-4-(3-butenyloxy)-butyrophenone as confirmed by elementary analysis.

Step B:

3-(2,3-Dichloro-4-butyrylphenoxy)propionic acid 2,3-Dichloro-4-(3-butenyloxy)butyrophenone (31.5 g, 0.11 mole) and benzyltriethylammonium chloride (2.3 g) in methylene chloride (350 ml) was added dropwise to a solution of potassium permanganate (45.8 g) in water (900 ml) at 5° C. The mixture was then stirred at 20° C. for 1.5 hours after which tests showed that the oxidation was complete. Sodium bisulfite and dilute hydrochloric acid was added until the color due to $KMnO_4$ disappeared. The mixture was filtered to remove a small amount of solid and the methylene chloride layer from the filtrate was separated. This layer was washed with water and then extracted with a dilute sodium hydroxide solution. The aqueous layer was poured into ice water containing dilute hydrochloric acid. The solid that separated was removed by filtration, washed with water, dried and recrystallized to give 9 g of 3-(2,3-dichloro-4-butyrylphenoxy)propionic acid, m.p. 138°–139°.

Anal. Calc'd for $C_{13}H_{14}Cl_2O_4$: C, 51.17; H, 4.62. Found: C, 51.11; H, 4.74.

Step C:

3-[2,3-Dichloro-4-(2-methylenebutyryl)phenoxy]propionic acid 3-(2,3-Dichloro-4-butyrylphenoxy)propionic acid (6.65 g, 0.022 mole), dimethylamine hydrochloride (12 g, 0.15 mole), paraformaldehyde (2.3 g, 0.077 equiv.) and acetic acid (1 ml) were mixed and stirred while heating on a steam bath for 2.5 hours. N,N-dimethylformamide (25 ml) was added to the mixture and stirring and heating continued for another 1.5 hours. The mixture was poured into ice water (600 ml) and the precipitate that formed removed by filtration, washed with water and dried. After recrystallization from butyl chloride, 58 g 3-[2,3-dichloro-4-(2-methylenebutyryl)phenoxy]propionic acid remained.

Anal. Calc'd for $C_{14}H_{14}Cl_2O_4$: C, 53.01; H, 4.45. Found: C, 52.88; H, 4.50.

EXAMPLE 2

Preparation of 4-[2,3-dichloro-4-(2-methylenebutyryl)phenoxy]butyric acid

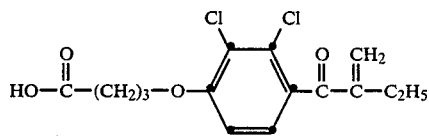

Step A:

4-(2,3-Dichloro-4-butyrylphenoxy)butyric acid

A mixture of 2,3-dichloro-4-butyrylphenol (69.9 g, 0.30 mole), potassium carbonate (75 g, 0.54 mole) and ethyl 4-bromobutyrate (87.8 g, 0.45 mole) in N,N-dimethylformamide (900 ml of sieve-dried material) were stirred and heated at 55°–60° C. for 16.5 hours. The mixture was then treated with 10 normal sodium hydroxide solution (120 ml) and water (600 ml) and stirring and heating at 100° C. maintained for 2 hours. The solution was cooled and poured into ice water (4 liters) containing concentrated hydrochloric acid (250 ml). The solid that separated was removed by filtration, washed with water and dried. The product (88 g) was recrystallized from butyl chloride (500 ml) to give 78.6 g of 4-(2,3-dichloro-4-butyrylphenoxy)butyric acid, m.p. 111°–113° C.

Anal. Calc'd for $C_{14}H_{16}Cl_2O_4$: C, 52.68; H, 5.05; Cl, 22.21. Found: C, 52.62; H, 5.09; Cl, 22.17.

Step B

4-[2,3-Dichloro-4-(2-methylenebutyryl)phenoxy]butyric acid 4-(2.3-Dichloro-4-butyrylphenoxy)butyric acid (71.8 g, 0.225 mole), paraformaldehyde (16.5 g, 0.549 equivalent), dimethylamine hydrochloride (82.0 g, 1.0 mole) and acetic acid (5.5 ml) were united and stirred on a steam bath for 7 hours. N,N-dimethylformamide (172 ml) was added and stirring and heating continued for another hour. The solution was then poured into cold 1 normal hydrochloric acid (1.5 liters) with stirring. The product that separated slowly solidified. This material was pulverized, filtered, washed with water and dried to give 70.8 g of product. This material was recrystallized from butyl chloride to give 4-[2,3-dichloro-4-(2-methylenebutyryl)phenoxy]butyric acid melting at 87°–89° C.

Anal. Calc'd for $C_{15}H_{16}Cl_2O_4$: C, 54.40; H, 4.87; Cl, 21.41. Found: C, 54.03; H, 4.98; Cl, 21.60.

EXAMPLE 3

Preparation of 4-[2,3-dichloro-4-(2-methylenevaleryl)phenoxy]butyric acid

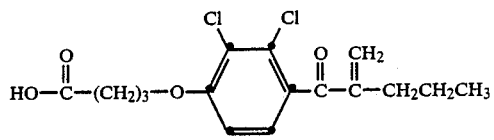

STEP A 4-(2,3-Dichloro-4-valerylphenoxy)butyric acid

By conducting the reaction as described in Example 2, Step A, except that an equimolar amount of 2,3-dichloro-4-valerylphenol was substituted for the 2,3-dichloro-4-butyrylphenol, there was obtained 4-(2,3-dichloro-4-valerylphenoxy)butyric acid, m.p. 92°–94° C.

Anal. Calc'd. for $C_{15}H_{18}Cl_2O_4$: C, 54.07; H, 5.45. Found: C, 54.63; H, 5.63.

Step B

4-[2,3-Dichloro-4-(2-methylenevaleryl)phenoxy]butyric acid

By conducting the reaction as described in Example 2, Step B, except that an equimolar amount of 4-(2,3-dichloro-4-valerylphenoxy)butyric acid was substituted for the 4-(2,3-dichloro-4-butyrylphenoxy)butyric acid, there was obtained 4-[2,3-dichloro-4-(2-methylenevaleryl)phenoxy]butyric acid, m.p. 85°–87° C.

Anal. Calc'd for $C_{16}H_{18}Cl_2O_4$: C, 55.67; H, 5.26. Found: C, 56.02; H, 5.34.

EXAMPLE 4

Preparation of 5-[2,3-dichloro-4-(2-methylenebutyryl)phenoxy]valeric acid

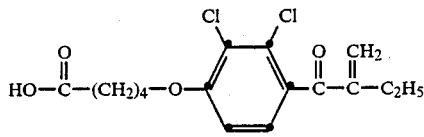

Step A 5-(2,3-Dichloro-4-butyrylphenoxy)valeric acid

A mixture of 2,3-dichloro-4-butyrylphenol (7 g, 0.03 mole), potassium carbonate (7.5 g, 0.054 mole) and ethyl 5-bromovalerate (9.5 g, 0.045 mole) in N,N-dimethylformamide (60 ml) were stirred and heated at 60° C. for 3 hours. The mixture was treated with 10 normal sodium hydroxide (12 ml) and water (50 ml), then stirred and heated on a steam bath for 2.5 hours. The solution was poured into ice water containing hydrochloric acid. The solid that separated was removed by filtration, washed with water and dried. The product (9.8 g) was recrystallized from butyl chloride to give 5-(2,3-dichloro-4-butyrylphenoxy)valeric acid, m.p. 102°–103° C.

Anal. Calc'd for $C_{15}H_{18}Cl_2O_4$: C, 54.07; H, 5.45. Found: C, 54.09; H, 5.38.

Step B

5-[2,3-Dichloro-4-(2-methylenebutyryl)phenoxy]valeric acid 5-(2,3-Dichloro-4-butylrylphenoxy)valeric acid (9.8 g, 0.029 mole), dimethylamine hydrochloride (15 g, 0.184 mole), paraformaldehyde (2.8 g, 0.09 equivalent) and acetic acid (1 ml) were united and stirred and heated on a steam bath for 3 hours. N,N-dimethylformamide (30 ml) was added and stirring and heating continued for another two hours. The reaction mixture was then poured into ice water and the solid that separated was removed by filtration, washed with water and dried. After recrystallization from butyl chloride the 5-[2,3-dichloro-(2-methylenebutyryl)phenoxy]valeric acid (5.4 g) melted at 107°–109° C.

Anal. Calc'd for $C_{16}H_{18}Cl_2O_4$: C, 55.66; H, 5.26. Found: C, 55.62; H, 5.31.

EXAMPLE 5

Preparation of 6-[2,3-dichloro-4-(2-methylenebutyryl)phenoxy]hexanoic acid

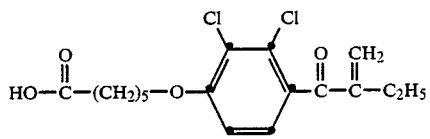

STEP A 6-(2,3-Dichloro-4-butyrylphenoxy)hexanoic acid

A mixture of 2,3-dichloro-4-butyrylphenol (7 g, 0.03 mole), potassium carbonate (7.5 g, 0.054 mole) and ethyl 6-bromohexanoate (10.25 g, 0.045 mole) in N,N-dimethylformamide (60 ml) was stirred and heated at 65° C. for 2.5 hours. The mixture was treated with 10 normal sodium hydroxide (12 ml) and water (50 ml), then stirred and heated on a steam bath for 2.5 hours. The reaction mixture was poured into ice water containing hydrochloric acid. The solid that separated was removed by filtration, washed with water and dried to give 10 g of product. Recrystallization from butyl chloride gave 6-(2,3-dichloro-4-butyrylphenoxy)hexanoic acid, m.p. 94°–95° C.

Anal. Calc'd for $C_{16}H_{20}Cl_2O_4$: C, 55.34; H, 5.81. Found: C, 55.39; H, 5.84.

Step B

6-[2,3-Dichloro-4-(2-methylenebutyryl)phenoxy]hexanoic acid

A mixture of 6-(2,3-dichloro-4-butyrylphenoxy)hexanoic acid (9.5 g, 0.026 mole), dimethylamine hydrochloride (15 g, 0.184 mole), paraformaldehyde (2.8 g, 0.09 equiv.) and acetic acid (1 ml) were united and stirred and heated on a steam bath for two hours. The reaction mixture was treated with N,N-dimethylformamide (30 ml) and stirring and heating continued for another hour. The reaction mixture was poured into ice water and the solid that separated was removed by filtration, washed with water and dried. The yield was 9.2 g after recrystallization from butyl chloride the 6-[2,3-dichloro-4-(2-methylenebutyryl)phenoxy]hexanoic acid melted at 106°–107° C.

Anal. Calc'd for $C_{17}H_{20}Cl_2O_4$: C, 56.84; H, 5.61. Found: C, 57.20; H, 5.75.

EXAMPLE 6

Preparation of 1-[2,3-dichloro-4-(2-methylenebutyryl)phenoxy]cyclobutane-1-carboxylic acid

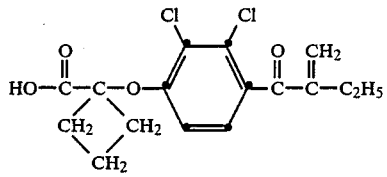

Step A

1-(2,3-Dichloro-4-butyrylphenoxy)cyclobutane-1-carboxylic acid

A mixture of 2,3-dichloro-4-butylrylphenol (7 g, 0.03 mole), ethyl α-bromocyclobutanecarboxylate (10.23 g, 0.049 mole) and potassium carbonate (7.5 g, 0.054 mole) in N,N-dimethylformamide (60 ml) was stirred and heated at 65° C. for 18 hours. The reaction mixture was poured into ice water and the resulting mixture was extracted with ether. The ether extract was washed with a 1% sodium hydroxide solution, then with water and finally dried over MgSO4. The ether was evaporated in vacuo and the residue treated with acetic acid (60 ml) and 5% hydrochloric acid (15 ml). The mixture was stirred and refluxed overnight. The solvents were evaporated in vacuo. The residue was chromatographed over a column containing silica gel (140 g) using methylene chloride/tetrahydrofuran/acetic acid 50/1/1 as the eluent. The pertinent fractions were united, treated with toluene and evaporated in vacuo to obtain 1-(2,3-dichloro-4-butyrylphenoxy)cyclobutane-1-carboxylic acid as a liquid whose identity was confirmed by NMR and purity by thin layer chromatography.

Step B

1-[2,3-Dichloro-4-(2-methylenebutyryl)phenoxy]cyclobutane-1-carboxylic acid A mixture of 1-(2,3-dichloro-4-butyrylphenoxy)cyclobutane-1-carboxylic acid (4 g, 0.012 mole), dimethylamine hydrochloride (5.5 g, 0.067 mole), paraformaldehyde (1.2 g, 0.04 equiv.) and acetic acid (0.3 ml) were stirred and heated on a steam bath for 2.25 hours. N,N-dimethylformamide (30 ml) was added and stirring and heating was continued for another 2 hours. The mixture was poured into ice water and extracted with ether. The ether layer was washed with water and then with brine and finally dried over MgSO4. The solution was treated with p-xylene and the solvents were removed in vacuo. The resulting residue was recrystallized from hexane to give 1-[2,3-dichloro-4-(2-methylenebutyryl)phenoxy]cyclobutane-1-carboxylic acid, m.p. 120° C.

Anal. Calc'd for $C_{16}H_{16}Cl_2O_4$: C, 55.99; H, 4.70. Found: C, 56.09; H, 4.80.

EXAMPLE 7

Preparation of 1-[2,3-dichloro-4-(2-methylenevaleryl)phenoxy]cyclobutane-1-carboxylic acid

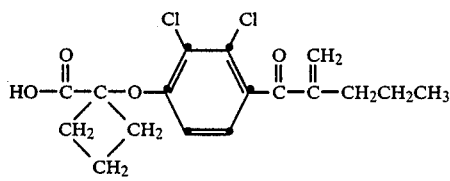

Step A

1-(2,3-Dichloro-4-valerylphenoxy)cyclobutane-1-carboxylic acid

By conducting the reaction as described in Example 6, Step A, except that an equimolar amount of 2,3-dichloro-4-valerylphenol was used in place of the 2,3-dichloro-4-butyrylphenol, there was obtained 1-(2,3-dichloro-4-valerylphenoxy)cyclobutane-1-carboxylic acid.

Step B

1-[2,3-Dichloro-4-(2-methylenevaleryl)phenoxy]cyclobutane-1-carboxylic acid By conducting the reaction as described in Example 6, Step B, except that an equimolar amount of 1-(2,3-dichloro-4-valerylphenoxy)cyclobutane-1-carboxylic acid was used in place of the 1-(2,3-dichloro-4-butyrylphenoxy)cyclobutane-1-carboxylic acid, there is obtained 1-[2,3-dichloro-4-(2-methylenevaleryl)phenoxy]cyclobutane-1-carboxylic acid, m.p. 105°–106° C.

Anal. Calc'd. for $C_{17}H_{18}Cl_2O_4$: C, 57.16; H, 5.05. Found: C, 57.46; H, 5.15.

EXAMPLE 8

Preparation of 2-[2,3-dichloro-4-(2-methylenebutyryl)-phenoxy]-2-methylpropionic acid

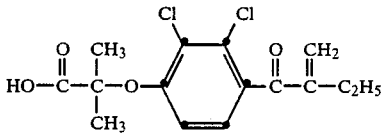

Step A

2-(2,3-Dichloro-4-butyrylphenoxy)-2-methylpropionic acid

A mixture of 2,3-dichloro-4-butyrylphenol (15 g, 0.064 mole), acetone (140 ml) and sodium hydroxide (14.5 g, 0.36 mole) was stirred and heated to reflux. Chloroform (12 g, 0.1 mole) was added to the mixture dropwise over a period of 15 minutes. Refluxing was continued for 3 hours and the acetone was evaporated in vacuo. The residue was treated with ice water containing hydrochloric acid. The produce was extracted with ether. The ether extract was washed with water, then with brine and finally dried over MgSO$_4$. The ether was evaporated in vacuo and the residue chromatographed on a column containing silica gel (320 g) and eluted with methylene chloride/tetrahydrofuran/acetic acid 50/1/1. The appropriate fractions were combined and evaporated in vacuo to give 10 g of 2-(2,3-dichloro-4-butyrylphenoxy)-2-methylpropionic acid which was identified by NMR and the purity confirmed by thin layer chromatography.

Step B

2-[2,3-Dichloro-4-(2-methylenebuytyryl)phenoxy]-2-methylpropionic acid

A mixture of 2-(2,3-dichloro-4-butyrylphenoxy)-2-methylpropionic acid (10 g, 0.031 mole), dimethylamine hydrochloride (15 g, 0.18 mole), paraformaldehyde (3 g, 0.10 equiv.) and acetic acid (0.6 ml) was stirred and heated on a steam bath for two hours. N,N-dimethylformamide (30 ml) was added and stirring and heating was continued for another two hours. The mixture was poured into ice water which was then extracted with ether. The ether extract was washed with water, then brine and finally dried over MgSO$_4$. The ether was evaporated in vacuo and the residue recrystallized from cyclohexane to give 6.3 g 2-[2,3-dichloro-4-(2-methylenebutyryl)phenoxy]-2-methylpropionic acid, m.p. 88°-89° C.

Anal. Calc'd for $C_{15}H_{16}Cl_2O_4$: C, 54.40; H, 4.87. Found: C, 54.71; H, 5.05.

EXAMPLE 9

An example of extracorporeal treatment will be considered.

One pint of blood from a homozygous patient's cells is removed and washed under sterile conditions with a 1 to 3 mM solution of the sodium salt of 4-[2,3-dichloro-4-(2-methylenebutyryl)phenoxy]butyric acid,

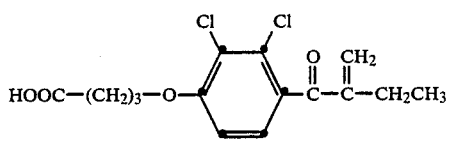

This washing is performed until the hemoglobin S is substantially completely converted to the new species having the sodium salt of the compound bound to the hemoglobin. This may be accomplished by washing the cells with about 4 to 6 liters of a 1 to 3 mM solution of the sodium salt of the compound. The reaction is monitored by the electrophoresis of a blood sample which demonstrates the percentage of conversion to the new hemoglobin derivative. The treated cells are then washed thoroughly with isotonic saline until substantially all of the excess and lightly bound drug is removed from the hemoglobin and the red cell membranes. The treated blood may then be reconstituted with plasma or nutrients or given directly to the patient.

The solubility assay (C$_{sat}$ assay) measures the ability of a compound to increase solubility of sickle hemoglobin (HbS). At low concentrations (5 mM), the sodium salt of 4-[2,3-dichloro-4-(2-methylenebutyryl)phenoxy]butyric acid exhibited a higher solubility ratio than other antisickling agents, such as, dichlorobenzyloxyacetic acid and p-bromobenzyloxyacetic acid. The higher the ratio, the higher the activity of the compound. Chromatographic separation confirmed the fact that desired tight covalent binding between the HbS and the therapeutic agent had occurred. Tests of transport across erythrocyte membranes confirmed the ability of the agent to cross the red blood cell membrane and react with hemoglobin.

It is believed that the compound functions by covalently bonding to the hemoglobin at two locales and forms a new kind of hemoglobin which does not sickle. This is not true of clofibric acid or other phenoxy alkanoic acids.

The process may be practiced extracorporeally although other means of administering the medication such as orally may be employed. The presently preferred oral dosage is about 50 mg to 2.5 g/day.

EXAMPLE 10

| Dry filled capsules containing 150 mg of active ingredient | |
|---|---|
| | Per Capsule |
| 4-[2,3-Dichloro-4-(2-methylenebutyryl)phenoxy]butyric acid | 150 mg |
| Lactose | 447 mg |
| Magnesium stearate | 3 mg |
| Capsule (size no. 000) | 600 mg |

4-[2,3-Dichloro-4-(2-methylenebutyryl)phenoxy]butyric acid is reduced to a No. 60 powder and then lactose and magnesium stearate are passed through a No. 60 bolting cloth onto the powder and the combined ingredients admixed for 10 minutes and then filled into a No. 1 dry gelatin capsule.

Similar dry-filled capsules can be prepared by replacing the active ingredient of the above example by any of the other compounds of this invention.

EXAMPLE 11

Parenteral Solution of Sodium 3-[2,3-Dichloro-4-(2-methylenebutyryl)phenoxy]propionate 25 mg of 3-[2,3-dichloro-4-(2-methylenebutyryl)phenoxy]propionic acid is dissolved in 3.1 ml of 0.1N sodium bicarbonate and sufficient isotonic buffer to make a final volume of 10 ml. The water from all sources was pyrogen-free. The solution is sterilized by filtration.

EXAMPLE 12

Parenteral Solution of Sodium 2-[2,3-Dichloro-4-(2-methylenebutyryl)phenoxy]-2-methylpropionate 250 mg of 2-[2,3-dichloro-4-(2-methylenebutyryl)phenoxy]methylpropionic acid is dissolved in 31 ml of 0.1N sodium bicarbonate and sufficient isotonic buffer to make a final volume of 100 ml. The water from all sources was pyrogen-free. The solution is sterilized by filtration.

EXAMPLE 13

Parenteral Solution of Sodium 4-[2,3-dichloro-4-(2-methylenevaleryl)phenoxy]butyrate 250 mg of 4-[2,3-dichloro-4-(2-methylenevaleryl)phenoxy]butyric acid is dissolved in 62 ml of 0.1N sodium bicarbonate and sufficient isotonic buffer to make a final volume of 100 ml. The water from all sources was pyrogen free. The solution is sterilized by filtration.

EXAMPLE 14

Parenteral Solution of Sodium 1-[2,3-Dichloro-4-(2-methylenevaleryl)phenoxy]cyclobutane-1-carboxylate 200 mg of 1-[2,3-dichloro-4-(2-methylenevaleryl)phenoxy]cyclobutane-1-carboxylic acid is dissolved in 31 ml of 0.1N sodium bicarbonate and sufficient isotonic buffer to make a final volume of 100 ml. The water from all sources was pyrogen free. The solution is sterilized by filtration.

EXAMPLE 15

Sterile Solution of Sodium 1-[2,3-Dichloro-4-(2-methylenebutyryl)phenoxy]cyclobutane-1-carboxylate for Extracorporeal Treatment of Red Blood Cells from Patients with Sickle Cell Anemia 0.103 g of 1-[2,3-Dichloro-4-(2-methylenebutyryl)phenoxy]cyclobutane-1-carboxylic acid is dissolved 33 ml of 0.1N sodium bicarbonate and with isotonic saline to make a final volume of 100 ml. The water from all sources was pyrogen free. The solution is sterilized by filtration. This solution is 3 mM in active antisickling agent.

It will be appreciated that the present invention provides a method for treatment of sickle cell anemia patients so as to resist undesired sickle cell anemia crisis. The method may advantageously be employed as a prophylactic.

Whereas particular embodiments of the invention have been described above for purposes of illustration, it will be evident to those skilled in the art that numerous variations of the details may be made without departing from the invention as defined in the appended claims.

EXAMPLE 16

In order to confirm the effectiveness of these compounds in reducing the effect of sickle cell anemia, tests were performed. The materials were tested according to the assay ($C_{sat}$) developed by Hofrichter et al. (J. Hofrichter, P. D. Ross and W. A. Eaton, *Proc. Natl. Acad. Sci.*, U.S.A. 73, 30–35, 1976). This assay involves deoxygenation of concentrated sickle hemoglobin with dithionite in the presence of different concentrations of the drugs being tested. Samples are then sealed in quartz epr tubes under anaerobic conditions and spun at about 150,000 g for about 2½ hours at about 35° C. in an ultracentrifuge. This procedure pellets the polymerized HbS (sickle hemoglobin) to the bottom of the tubes and the supernatant (soluble HbS) is measured in the laboratory as the cyanmethemoglobulin derivative. The more active the compound the greater the solubility of HbS and the smaller the pellet size. Activity is reported as a ratio of the HbS solubility with the particular drug to HbS solubility with no drug, i.e. control. The higher the ratio the greater degree of activity of the drug. The numbers in parenthesis are the percent increase in solubility of HbS; again, the higher the number, the greater the activity. The results of representative compounds from the Examples are shown in Table I as typical of the compounds of the invention.

TABLE I

| Example Number of the Compound Tested | Ratio of the HbS Solubility with the Drug Compared to HbS Solubility Without Drug (% increase in Solubility) at the Concentrations Indicated | | | |
|---|---|---|---|---|
| | 3 mM | 5 mM | 7 mM | 9 mM |
| 1 | 1.112 (26) | 1.145 (33) | 1.188 (43) | 1.302 (69) |
| 2 | 1.092 (22) | 1.112 (27) | 1.157 (37) | 1.196 (46) |
| 3 | 1.075 (18) | 1.159 (37) | 1.197 (46) | 1.219 (51) |
| 4 | 1.081 (21) | 1.129 (34) | 1.200 (52) | 1.308 (80) |
| 5 | 1.063 (13) | 1.086 (18) | 1.125 (26) | 1.164 (35) |
| 6 | 1.080 (19) | 1.126 (30) | 1.147 (34) | 1.202 (48) |
| 7 | 1.057 (14) | 1.122 (30) | 1.104 (26) | 1.156 (39) |
| 8 | 1.050 (11) | 1.094 (21) | 1.183 (41) | 1.237 (53) |

What is claimed is:

1. A compound of the general formula and pharmaceutically acceptable salts thereof:

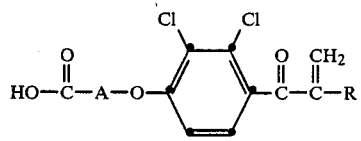

wherein R is ethyl, propyl or isopropyl and A is —(CH$_2$)$_n$— or C(CH$_2$)$_3$ and n=4 or 5.

2. The compound of claim 1, which is 5-[2,3-dichloro-4-(2-methylenebutyryl)phenoxy]valeric acid.

3. The compound of claim 1, which is 6-[2,3-dichloro-4-(2-methylenebutyryl)phenoxy]hexanoic acid.

4. The compound of claim 1, which is 1-[2,3-dichloro-4-(2-methylenebutyryl)phenoxy]cyclobutane-1-carboxylic acid.

5. The compound of claim 1 which is 1-[2,3-dichloro-4-(2-methylenevaleryl)phenoxy]cyclobutane-1-carboxylic acid.

6. An antisickling pharmaceutical composition comprising a pharmaceutical carrier and an antisickling agent of the general formula and pharmaceutically acceptable salts thereof:

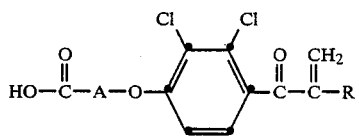

wherein R is ethyl, propyl or isopropyl and

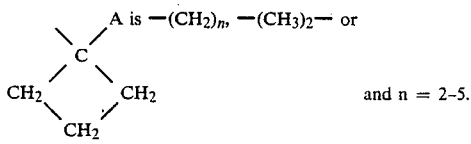

A is —(CH$_2$)$_n$, —(CH$_3$)$_2$— or  and n = 2-5.

7. A pharmaceutical composition of claim 6, wherein said antisickling agent is 3-[2,3-dichloro-4-(2-methylenebutyryl)phenoxy]propionic acid.

8. A pharmaceutical composition of claim 6, wherein said antisickling agent is 4-[2,3-dichloro-4-(2-methylenebutyryl)phenoxy]butyric acid.

9. A pharmaceutical composition of claim 6, wherein said antisickling agent is 5-[2,3-dichloro-4-(2-methylenebutyryl)phenoxy]valeric acid.

10. A pharmaceutical composition of claim 6, wherein said antisickling agent is 6-[2,3-dichloro-4-(2-methylenebutyryl)phenoxy]hexanoic acid.

11. A pharmaceutical composition of claim 6, wherein said antisickling agent is 2-[2,3-dichloro-4-(2-methylenebutyryl)phenoxy]-2-methylpropionic acid.

12. A pharmaceutical composition of claim 6, wherein said antisickling agent is 1-[2,3-dichloro-4-(2-methylenebutyryl)phenoxy]cyclobutane-1-carboxylic acid.

13. A pharmaceutical composition of claim 6, wherein said antisickling agent is 1-[2,3-dichloro-4-(2-methylenevaleryl)phenoxy]cyclobutane-1-carboxylic acid.

14. A pharmaceutical composition of claim 6, wherein said antisickling agent is 4-[2,3-dichloro-4-(2-methylenevaleryl)phenoxy]butyric acid.

* * * * *

UNITED STATES PATENT AND TRADEMARK OFFICE
CERTIFICATE OF CORRECTION

PATENT NO. : 4,731,473
DATED : March 15, 1988
INVENTOR(S) : E. J. Cragoe et al

It is certified that error appears in the above—identified patent and that said Letters Patent is hereby corrected as shown below: On the Title Page:

In the Heading at [73]

The assignee should be listed as "Merck and Co., Inc. and the University of Pittsburgh."

Signed and Sealed this

Ninth Day of August, 1988

Attest:

DONALD J. QUIGG

Attesting Officer

Commissioner of Patents and Trademarks